US 7,708,737 B2

(12) United States Patent  (10) Patent No.: US 7,708,737 B2
Kraft et al.                (45) Date of Patent:     May 4, 2010

(54) INTRAMEDULLAR DISTRACTION DEVICE WITH USER ACTUATED DISTRACTION

(75) Inventors: David Kraft, Rehovot (IL); Alexander Lev Rubinstein, Israeli (IL); Nissim Forte, Israeli (IL)

(73) Assignee: Intramed Systems Ltd, Netanya (IL)

( * ) Notice: Subject to any disclaimer, the term of this patent is extended or adjusted under 35 U.S.C. 154(b) by 728 days.

(21) Appl. No.: 11/456,881

(22) Filed: Jul. 12, 2006

(65) Prior Publication Data

US 2007/0016202 A1    Jan. 18, 2007

Related U.S. Application Data

(60) Provisional application No. 60/698,003, filed on Jul. 12, 2005.

(51) Int. Cl.
    *A61B 17/56* (2006.01)
(52) U.S. Cl. .............................. 606/63; 606/68; 606/320
(58) Field of Classification Search ............ 604/164.12; 606/55, 57, 58, 60, 62–64, 67, 68, 90, 105, 606/282; 74/141.5, 369, 40, 503, 66; *A61B 17/56, A61B 17/58; A61F 2/30*
    See application file for complete search history.

(56) References Cited

U.S. PATENT DOCUMENTS

| | | | | |
|---|---|---|---|---|
| 3,976,060 A | * | 8/1976 | Hildebrandt et al. | 606/241 |
| 4,615,338 A | * | 10/1986 | Ilizarov et al. | 606/58 |
| 4,644,943 A | * | 2/1987 | Thompson et al. | 606/64 |
| 5,074,882 A | | 12/1991 | Grammont et al. | 606/63 |
| 5,350,379 A | * | 9/1994 | Spievack | 606/63 |
| 5,505,733 A | * | 4/1996 | Justin et al. | 606/63 |
| 5,536,269 A | * | 7/1996 | Spievack | 606/63 |
| 5,626,579 A | * | 5/1997 | Muschler et al. | 606/60 |
| 5,672,177 A | | 9/1997 | Seldin | 606/71 |
| 5,961,553 A | | 10/1999 | Coty et al. | 606/62 |
| 6,033,412 A | * | 3/2000 | Losken et al. | 606/105 |
| 6,113,599 A | * | 9/2000 | Landsberger | 606/60 |
| 6,235,029 B1 | | 5/2001 | Faccioli et al. | 606/54 |
| 6,245,075 B1 | | 6/2001 | Betz et al. | 606/105 |
| 6,383,185 B1 | | 5/2002 | Baumgart | 606/63 |
| 6,416,516 B1 | | 7/2002 | Stauch et al. | 606/62 |
| 6,673,079 B1 | | 1/2004 | Kane | 606/105 |
| 6,730,087 B1 | | 5/2004 | Butsch | 606/57 |
| 6,736,818 B2 | | 5/2004 | Perren et al. | 606/63 |

(Continued)

FOREIGN PATENT DOCUMENTS

DE    4002400    8/1991

*Primary Examiner*—Eduardo C Robert
*Assistant Examiner*—Lynnsy Schneider
(74) *Attorney, Agent, or Firm*—D. Graeser Ltd.

(57) ABSTRACT

An intramedullar distraction device for bone elongation that is completely mechanical in operation, wherein a novel rotating button system allows inverting the device ratchet movement, thereby enabling the reduction of the length of the device, if needed, in order to offer the surgeon operating flexibility before finally anchoring the device on the bone. Furthermore, a locking system allows for locking the ratchet once the desired elongation has been reached, thus avoiding potential mistaken elongations. In addition, a unique alignment hole provides a simple, precise tool to easily and correctly align the device within the bone. The present device operates without the assistance of external mechanisms, motors, or tools, and once inserted, the user can actuate the device without assistance. This device is available in a wide variety of diameters and lengths, and is useful in all long bones.

16 Claims, 6 Drawing Sheets

U.S. PATENT DOCUMENTS

| | | |
|---|---|---|
| 6,918,910 B2 | 7/2005 | Smith et al. .................... 606/60 |
| 7,063,706 B2 | 6/2006 | Wittenstein ................... 606/90 |
| 2004/0030395 A1 | 2/2004 | Blunn et al. ............. 623/18.12 |
| 2004/0193266 A1* | 9/2004 | Meyer ..................... 623/16.11 |
| 2005/0107787 A1* | 5/2005 | Kutsenko ..................... 606/57 |
| 2005/0246034 A1* | 11/2005 | Soubeiran ................ 623/23.45 |

* cited by examiner

INTRAMEDULLAR DISTRACTION DEVICE WITH USER ACTUATED DISTRACTION

FIELD OF INVENTION

This invention relates generally to surgical devices used to mend bones, and specifically to intramedullar devices used to lengthen or mend long bones.

BACKGROUND OF THE INVENTION

There are many reasons why a bone or limb may need to be lengthened, such as congenital bone disorders, disruptions in the bone's normal development, traumas, and many other medical problems. The resulting difference in the length of the limbs needs to be resolved in order to provide an acceptable level of quality of life for the patient.

Today, bone elongation is a common procedure in orthopedic medicine. The most realistic and the safest surgical options are based on the recently discovered phenomenon of "Callotasis", or "bone distraction".

In short, this means utilizing the natural healing process of the body that causes a bone that has been split in two to repair itself by creating new tissue to fill in the gap and heal the bone. In Callotasis, or bone distraction, the bone is progressively healed and lengthened by the slow distraction of the two split portions. At the end of the process, the new tissue consolidates into a perfect new bone.

Many related art devices, commonly referred to as "distractors", utilize said bone distraction phenomenon to lengthen various bones.

Older, more common devices are external to the body and comprise, for example, sets of external rings, strings, and pins installed around the limb being treated and connected to the bone portions through the soft tissues. Such devices cause a large amount of pain and inconvenience to the patient. Additionally, such devices penetrate through the soft tissues, causing many septic problems and repetitive infections. Furthermore, these external devices are ungainly and greatly restrict the patient's ability to move about freely.

More recently, the related art has attempted to provide a solution to these problems by various means, proposing to implant devices within the medullar cavity of the bone (intramedullar). In order to extend the devices and cause the desired bone lengthening, a mover is required. Different movers have been proposed. Illustrative of such attempts include German patent No. 4002400, which relates to an intramedullar locking pin with a spring mechanism that is adjustable from outside; U.S. Pat. No. 5,074,882, which discloses a nail for gradually lengthening long bones, wherein the bone is lengthened post-operatively by rotation of a distal part of the limb with respect to the proximal part of the limb; US patent Application No. 2004030395, which features a surgical distraction for applying extending or tensioning force non-invasively to a patient's skeleton which relies on a magnetic actuating means located externally of the patient; and U.S. Pat. No. 5,961,553, which relates to a device for elongating long bones that includes an electric motor as means for moving the extension.

Because of the reliance of such devices on external sources of actuation, patients face a number of new drawbacks from use of such intramedullar devices. Intramedullar devices tend to have a high cost and limited elongation capabilities. Physicians face difficulties in managing the treatment programs that require patients to arrive at the medical facility. Furthermore, in addition to requiring the patient be at a specific location in order to actuate the lengthening process, the external actuation means itself may restrict the patient's mobility.

In addition, related art simply does not provide an inexpensive, effective solution that is comfortable for the patient and that provides an easily managed follow-up program, wherein the device is both completely internal and a completely mechanical device according to the principle of the present invention.

SUMMARY OF INVENTION

The invention presented herein addresses the above-mentioned drawbacks of related art intramedullar distraction devices by providing a device with a number of novel improvements.

The present invention describes a novel, implantable, intramedullar distraction device for bone elongation that is introduced in a single surgical procedure. The elongation of the bone occurs by stretching the bone according to the previously described Callotasis phenomenon. Once inserted, the user is able to operate the device without assistance. The frequency of actuation is determined and monitored by the treating physician. After the bone has been lengthened and has completely consolidated itself, the device is easily removed in another single surgical procedure.

The device presented herein is operated mechanically by means of a subcutaneous button that is actuated by the patient several times a day, without assistance from the doctor.

A unique feature of the device is that it is mechanical in nature and completely self-contained, that is, this device operates without the assistance of external mechanisms or tools. Another unique feature of this device is the ratchet assembly that allows for this completely mechanical operation. Furthermore, the device relies on no connection to any external power sources for its operation, unlike related art apparatuses.

A further unique feature of the present invention is the alignment holes that provide the doctor with a simple but precise tool for ensuring that the device is properly aligned within the bone.

Yet another novel feature of the present invention is the ability not only to lengthen the distraction section of the device, but also to shorten the same section. This feature is particularly useful during insertion and removal the present invention.

Yet another advantage is that this new device is available in a variety of diameters and lengths, and is useful in all long bones.

Furthermore, because of the fully mechanical design that includes minimal moving parts and no external components, the present invention offers an highly reliable, inexpensive, comfortable, and relatively painless solution to bone elongation that allows the patient greater freedom of movement, decreased risk of infection, shorter hospital stays, and faster recovery time.

BRIEF DESCRIPTION OF DRAWINGS

The subject matter regarded as the invention will become more clearly understood in light of the ensuing description of embodiments herein, given by way of example and for purposes of illustrative discussion of the present invention only, with reference to the accompanying drawings, wherein.

Figure 1:
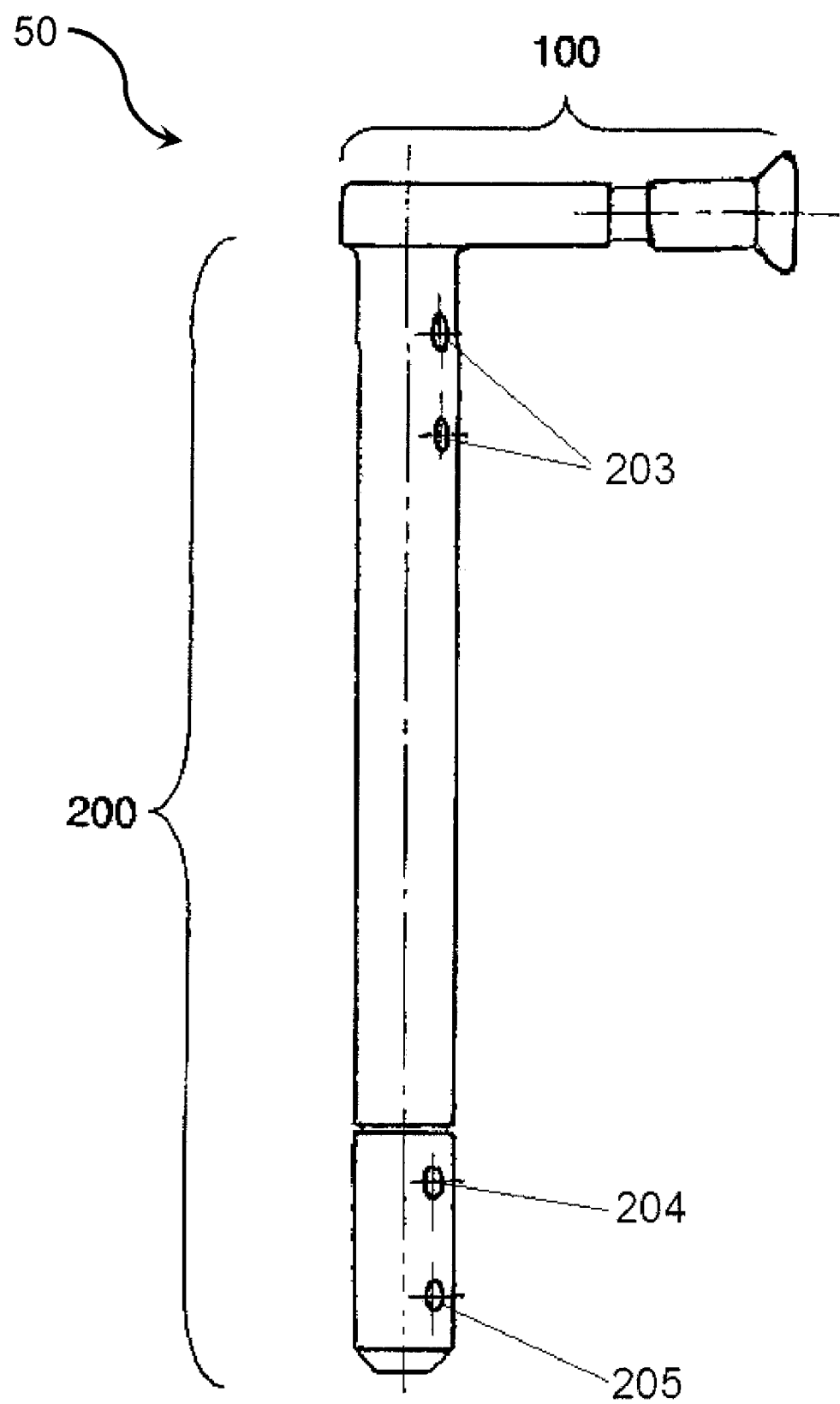
FIG. 1 is an elevated view of an embodiment of the present invention.

The drawings together with the description make apparent to those skilled in the art how the invention may be embodied in practice.

No attempt is made to show structural details of the invention in more detail than is necessary for a fundamental understanding of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DESCRIPTION OF THE EMBODIMENTS OF THE INVENTION

An embodiment is an example or implementation of the inventions. The various appearances of "one embodiment," "an embodiment" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "one embodiment", "an embodiment", "some embodiments" or "other embodiments" means that a particular feature, structure, or characteristic described in connection with the embodiments is included in at least one embodiments, but not necessarily all embodiments, of the inventions.

It is understood that the phraseology and terminology employed herein is not to be construed as limiting and are for descriptive purpose only.

The principles and uses of the teachings of the present invention may be better understood with reference to the accompanying description, figures, and examples.

It is to be understood that the details set forth herein do not construe a limitation to an application of the invention.

Furthermore, it is to be understood that the invention can be carried out or practiced in various ways and that the invention can be implemented in embodiments other than the ones outlined in the description below.

It is to be understood that the terms "including", "comprising", "consisting" and grammatical variants thereof do not preclude the addition of one or more components, features, steps, or integers or groups thereof and that the terms are to be construed as specifying components, features, steps or integers.

The phrase "consisting essentially of", and grammatical variants thereof, when used herein is not to be construed as excluding additional components, steps, features, integers or groups thereof but rather that the additional features, integers, steps, components or groups thereof do not materially alter the basic and novel characteristics of the claimed composition, device or method.

If the specification or claims refer to "an additional" element, that does not preclude there being more than one of the additional element.

It is to be understood that where the claims or specification refer to "a" or "an" element, such reference is not be construed that there is only one of that element.

It is to be understood that where the specification states that a component, feature, structure, or characteristic "may", "might", "can" or "could" be included, that particular component, feature, structure, or characteristic is not required to be included.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

Methods of the present invention may be implemented by performing or completing manually, automatically, or a combination thereof, selected steps or tasks.

The term "method" refers to manners, means, techniques and procedures for accomplishing a given task including, but not limited to, those manners, means, techniques and procedures either known to, or readily developed from known manners, means, techniques, and procedures by practitioners of the art to which the invention belongs.

The descriptions, examples, methods, and materials presented in the claims and the specification are not to be construed as limiting but rather as illustrative only.

Meanings of technical and scientific terms used herein are to be commonly understood as by one of ordinary skill in the art to which the invention belongs, unless otherwise defined.

The present invention can be implemented in the testing or practice with methods and materials equivalent or similar to those described herein.

The terms "bottom", "below", "top" and "above" as used herein do not necessarily indicate that a "bottom" component is below a "top" component or that a component that is "below" is indeed "below" another component or that a component that is "above" is indeed "above" another component. As such, directions, components or both may be flipped, rotated, moved in space, placed in a diagonal orientation or position, placed horizontally, or vertically, or similarly modified. Accordingly, it will be appreciated that the terms "bottom", "below", "top" and "above" may be used herein for exemplary purposes only, to illustrate the relative positioning or placement of certain components, to indicate a first and a second component or to do both.

Any publications, including patents, patent applications and articles, referenced or mentioned in this specification are herein incorporated in their entirety into the specification, to the same extent as if each individual publication was specifically and individually indicated to be incorporated herein. In addition, citation or identification of any reference in the description of some embodiments of the invention shall not be construed as an admission that such reference is available as prior art to the present invention.

The present invention describes an implantable, intramedullar distraction device for bone elongation. A feature of this intramedullar device is the ratchet assembly that allows for complete mechanical operation by the patient, wherein the patient may operate the intramedullar device by depressing a button. Another feature of the intramedullar device is that because it is mechanical in nature and completely self-contained, said intramedullar device may operate without the assistance of external mechanisms, motors, or tools. Once inserted, the user is able to operate the intramedullar device without assistance. Unlike related art, thanks to the simplicity of the intramedullar device and therefore to the absence of cumbersome internal parts such as motors, batteries, magnetic devices, etc., this new intramedullar device is available in a large variety of diameters and lengths, and is useful in all of the long bones. Another feature of the present invention is an alignment hole that provides the doctor with a simple but precise tool for ensuring that the intramedullar device is properly aligned within the bone. A further feature of the intramedullar device is the ratchet mechanism that enables both the lengthening and shortening of the intramedullar device, thus providing greater flexibility to the physician during the crucial insertion and lengthening phase of the process. Another feature of the intramedullar device is that the actuation of said ratchet mechanism may be locked once elongation is complete, thus avoiding accidental lengthening of the bone by unwanted actuation of the button.

According to an embodiment of the present invention, an intramedullar device 50 comprises a ratchet assembly 100 and a nail assembly 200, as shown in FIG. 1. Ratchet assembly 100 houses the various components that operate intramedullar device 50, seen clearly in FIGS. 2, 5A, and 5B. The unique features of intramedullar device 50 enable the user to operate ratchet assembly 100 unassisted and without additional external mechanisms or devices. Nail assembly 200 houses the components necessary to carry out the bone distraction; these components are described in FIG. 4.

A subcutaneous button 115 is located at the outer most end of ratchet assembly 100. Once intramedullar device 50 is inserted, subcutaneous button 115 is positioned below and close to the surface of the skin, in a location that is comfortably accessible to the user. The user depresses subcutaneous button 115, according to a prescribed schedule defined by the medical doctor, in order to initiate the ratcheting action, thereby rotating a long screw 112.

Figure 3:
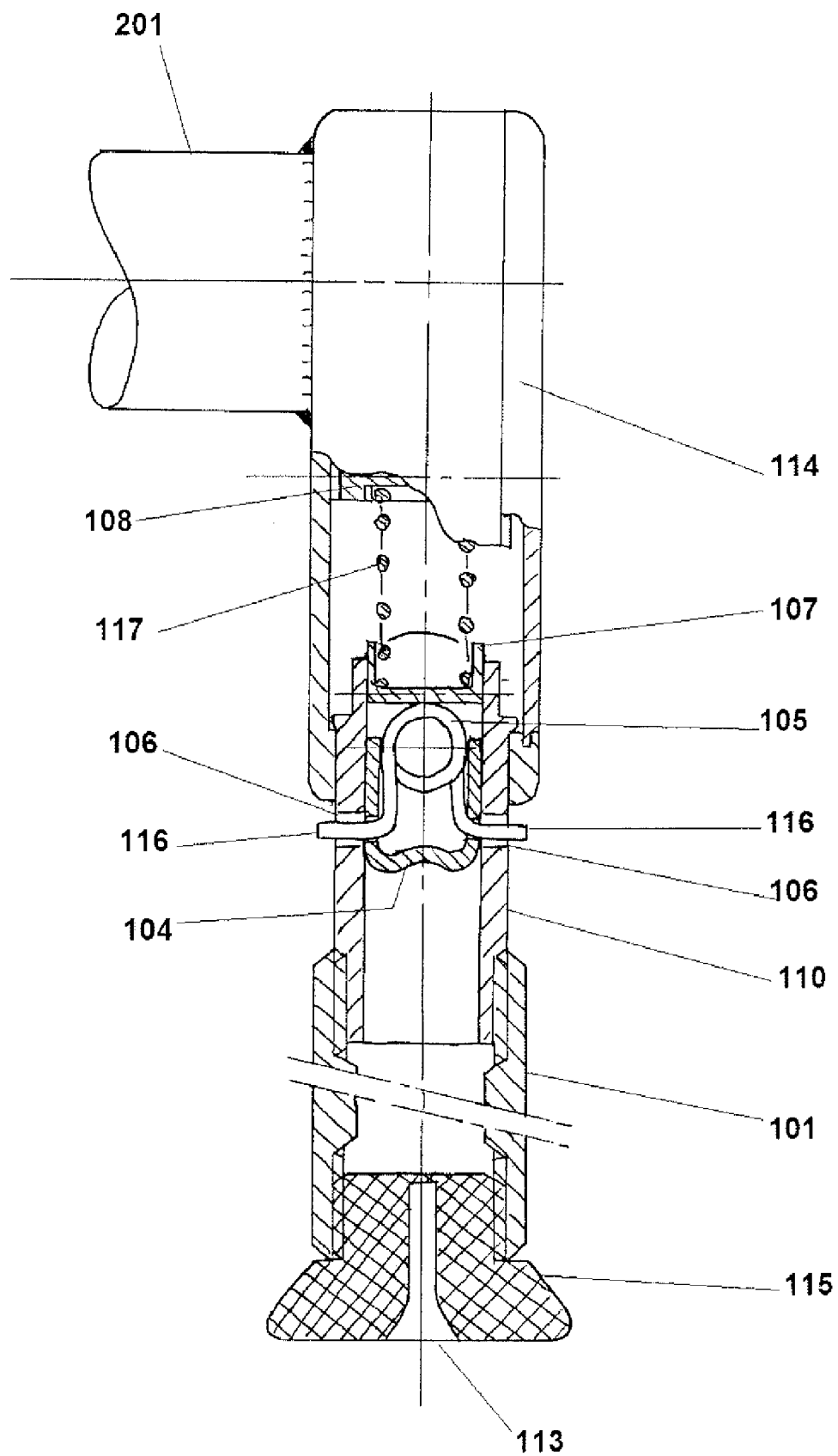
FIG. 3 is a sectional side view of the ratchet assembly of the embodiment of FIG. 1, in the locked position.

In the event that the length of ratchet assembly 100 is insufficient to correctly position subcutaneous button 115, there may be the option of extending subcutaneous button 115 to accommodate the thickness of the fat and skin by attaching a spacer 101, seen in FIG. 3, between a center chamber 110 and subcutaneous button 115.

According to embodiments, a funnel shaped opening 113 may be included at the terminal end of subcutaneous button 115. According to some embodiments, a needle or pin may be inserted into funnel shaped opening 113 in order to permanently lock the entire ratchet assembly 100.

Figure 2:
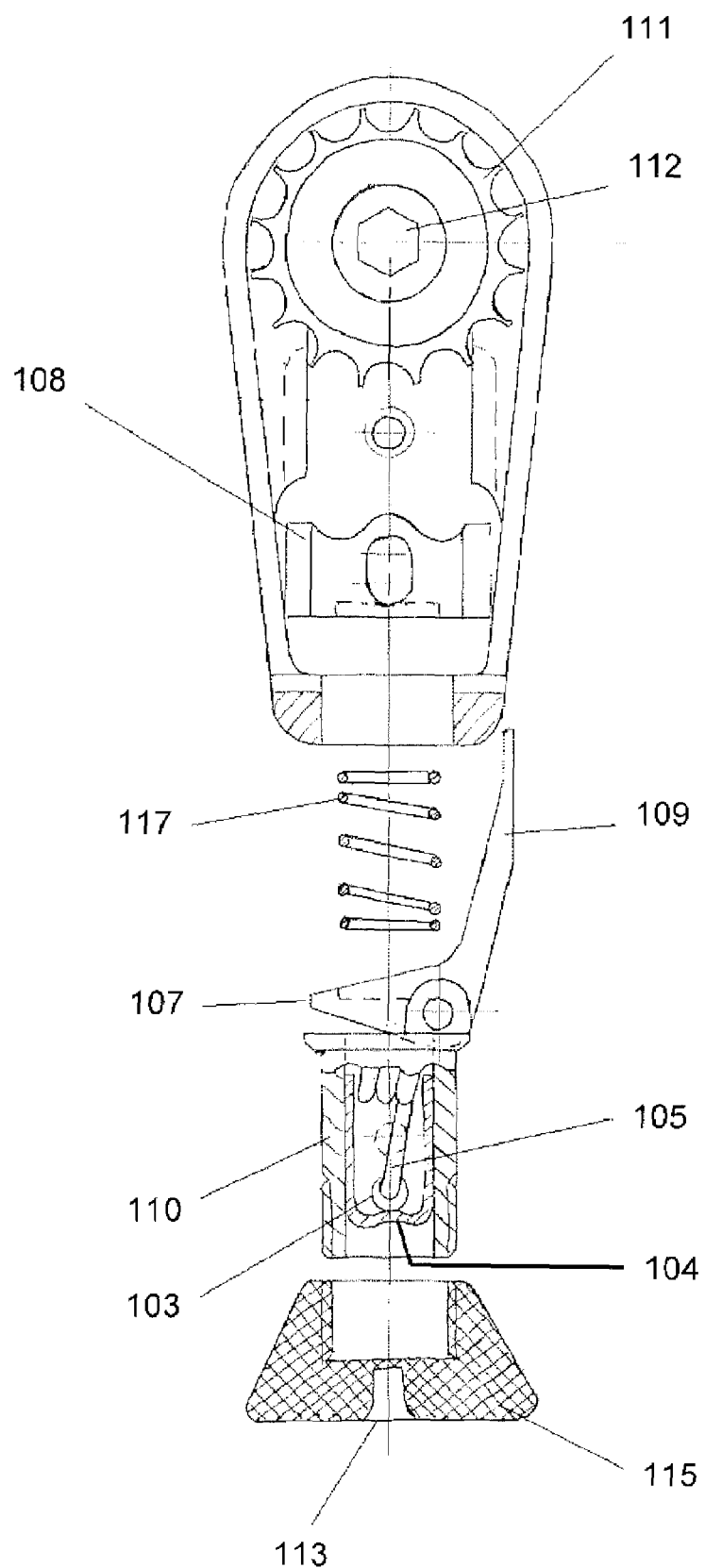
FIG. 2 is an exploded top view of a ratchet assembly of the embodiment of FIG. 1.

Subcutaneous button 115 connects to center chamber 110, which is situated between subcutaneous button 115 and the area housing a leverage mechanism 107, as seen in FIGS. 2 and 3. Housed within center chamber 110 are a cylinder-plate 104 and a locking spring 105. Center chamber 110 may be further equipped with at least two diametrically opposed holes 106. According to some embodiments, cylinder-plate 104 is an extruded, substantially U-shaped member. The end of cylinder-plate 104 closest to subcutaneous button 115 may be dimpled. Cylinder-plate 104 may be further equipped with at least two diametrically opposed holes 103. Cylinder-plate 104 may slide freely within center chamber 110. Locking spring 105 may be located within cylinder-plate 104. The ends 116 of locking spring 105 may be formed so as to protrude in an outwardly direction.

According to embodiments, while in an actuating position, ends 116 of locking spring 105 may sit inside holes 103 of cylinder-plate 104, compressed against the internal wall of center chamber 110, thus holding cylinder-plate 104 in place. According to embodiments, while in said actuating position, when cylinder-plate 104 is pushed by a needle inserted through funnel shaped opening 113, said cylinder-plate 104 moves forward inside center chamber 110, towards leverage mechanism 107 until holes 103 of cylinder-plate 104 align with holes 106 of center chamber 110. This movement frees ends 116 of locking spring 105, which enables ends 116 to move out into holes 106 of center chamber 110. This places intramedullar device 50 in a locked position, as shown in FIG. 3, thereby completely locking ratchet assembly 100.

According to embodiments, leverage mechanism 107 may be a rocker-type mechanism that spans the gap between center chamber 110 and a gear 111, as seen in FIGS. 2 and 3. The terminal end of leverage mechanism 107 is flexibly connected to center chamber 110. The second end of leverage mechanism 107 may include a pin 109. While intramedullar device 50 is in the actuating position, subcutaneous button 115, with or without spacer 101, may be depressed, which causes center chamber 110 to move forward and actuate leverage mechanism 107. When leverage mechanism 107 is thusly actuated, pin 109 of leverage mechanism 107 may connect with gear 111, causing gear 111 to rotate.

According to embodiments of the invention, when in the actuating position, fully depressing subcutaneous button 115 moves center chamber 110 forward. Leverage mechanism 107 may then be actuated by said center chamber 110. When moved forward by center chamber 110, leverage mechanism 107 may push pin 109 forward. Pin 109, in turn, may cause gear 111 and a long screw 112 to rotate a single click, thus altering the length of intramedullar device 50.

Figure 5A:
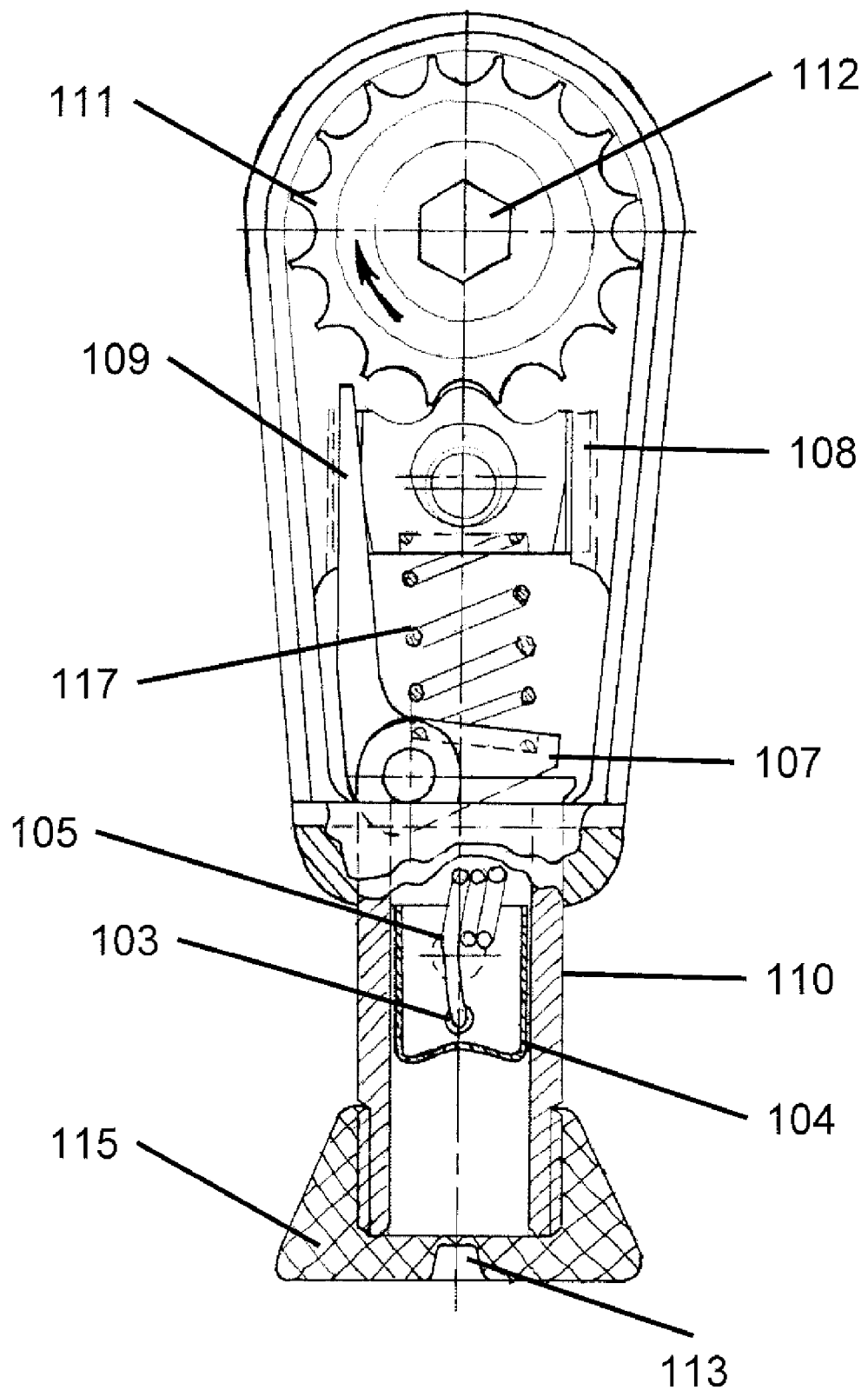
FIG. 5A is a sectional top view of the ratchet assembly of the embodiment of FIG. 1, configured for shortening.
Figure 5B:
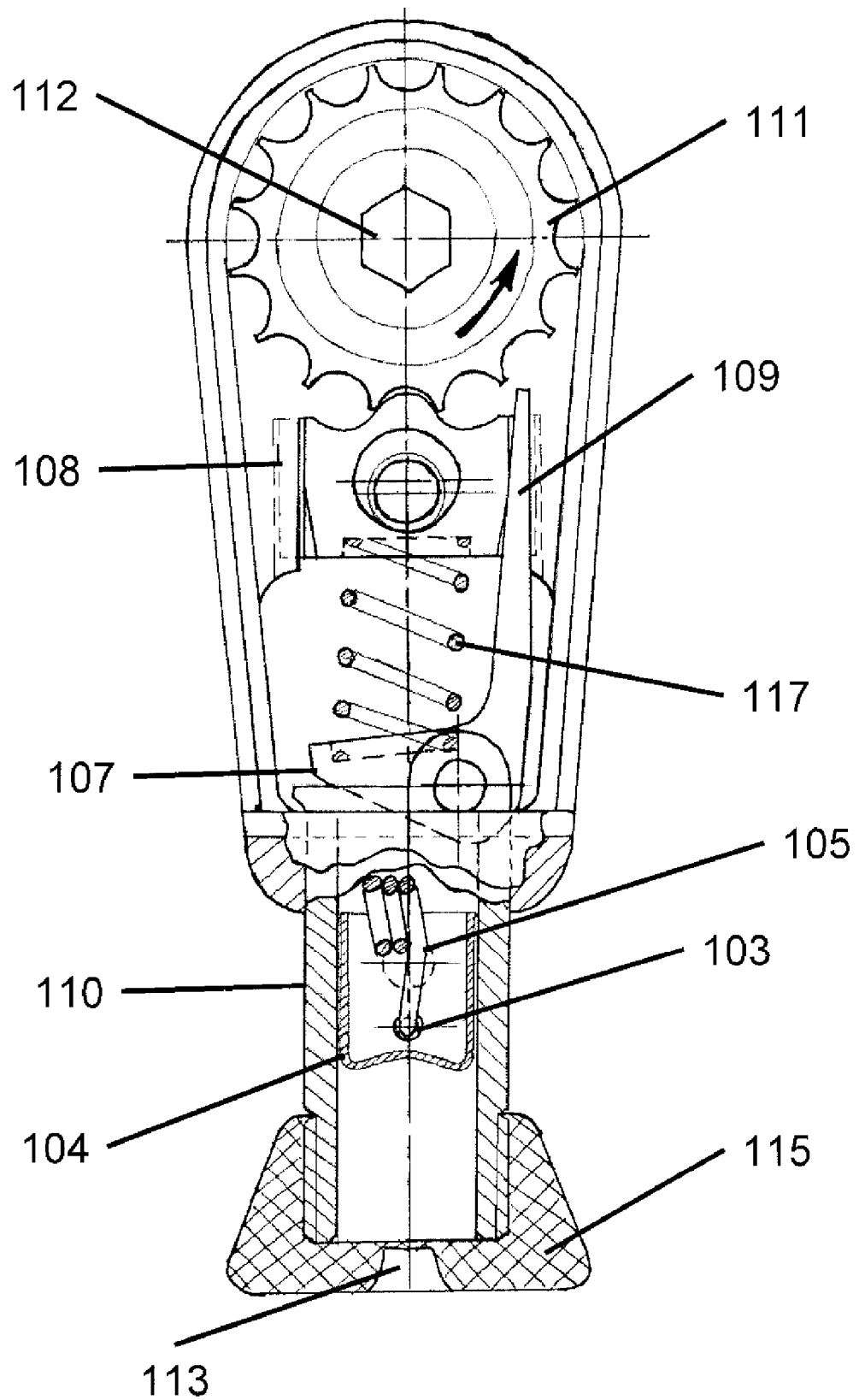
FIG. 5B is a sectional top view of the ratchet assembly of the embodiment of FIG. 1, configured for elongating.

A novel feature of the invention is that center chamber 110, together with leverage mechanism 107 and a main spring 117, may rotate, for example, 180 degrees around a longitudinal axis, allowing pin 109 to be positioned on the opposite side, relative to its original position, of ratchet assembly 100. As a result, gear 111 and consequently long screw 112, may turn in a direction opposite to the previous movement. For example, were intramedullar device 50 positioned for lengthening, as shown in FIG. 5B, rotating the above-referenced components would enable shortening the length of intramedullar device 50, as shown in FIG. 5A.

According to some embodiments, a floating stopper 108 may be mounted within ratchet assembly 100, between leverage mechanism 107 and gear 111, ensuring that gear 111 may always rotate in either of the desired directions. Thus, during the insertion and lengthening phase, when intramedullar device 50 is inserted into the bone and then extended, stopper 108 may ensure that the rotation of gear 111 and of long screw 112 is in a direction that causes the lengthening of intramedullar device 50, while at the same time preventing any motion of either gear 111 or long screw 112 in a reverse direction.

During said insertion and lengthening phase, circumstances may require that the initial length of intramedullar device 50 be adjusted. For example, a mistake may be made in estimating the required length, resulting in intramedullar device 50 being over-elongated prior to final positioning in the bone. According to some embodiments, the surgeon is optionally able to make use of an innovative and unique feature of the present invention, wherein intramedullar device 50 may be shortened prior to the final anchoring by rotating center chamber 110 as described above, and then pressing subcutaneous button 115 to turn gear 111 and long screw 112 in a direction that will reduce the length of intramedullar device 50. This bi-directional feature may also be used for other purposes, such as, but not limited to, assisting in the removal of intramedullar device 50 from the bone, where locking spring 105 mechanism has not been moved to a locked position.

Figure 4:
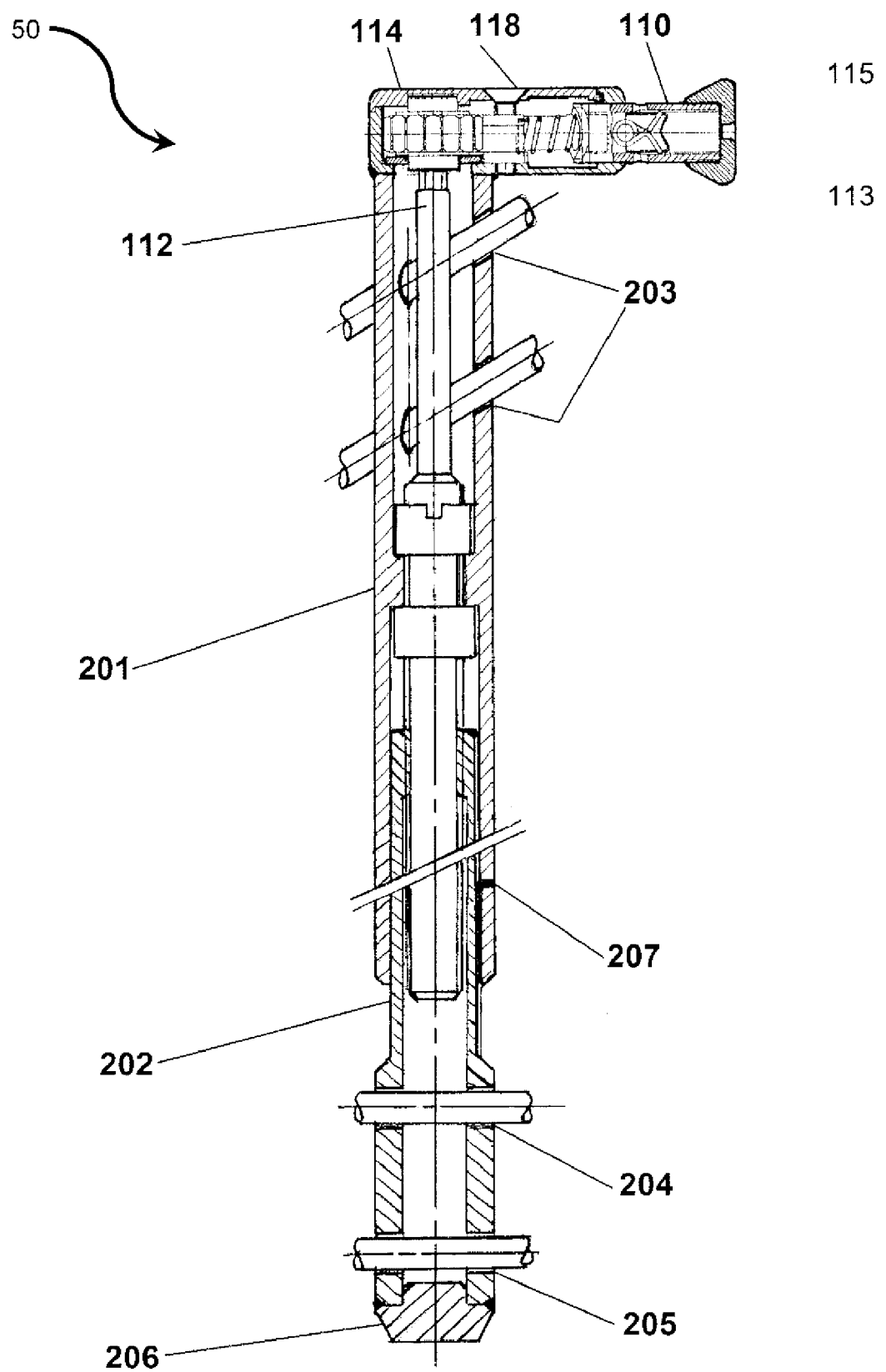
FIG. 4 is a sectional side view of the device of the embodiment of FIG. 1.

A ratchet cover 114, seen in FIG. 4, ensures that ratchet mechanism is scaled. A screw 118 holds ratchet cover 114 in place and ensures that leverage mechanism 107 remains in the desired position.

Ratchet assembly 100 is geared such that each depression of subcutaneous button 115 rotates long screw 112 an amount equivalent to one tooth on gear 111, providing very precise control of the extension activity.

The diameter of the gear 111 and the size and quantity of teeth on gear 111 may vary according to different embodiments of the present invention.

According to an embodiment of the present invention, the top of nail assembly 200 is rigidly connected to ratchet assembly 100, and at substantially a right angle. According to some other embodiments, nail assembly 200 may be connected to ratchet assembly 100 at greater or less than a right angle.

Nail assembly 200, shown in FIG. 4, like many known in the art devices, is a long, substantially tubular shaped metal piece that is designed to be inserted into the prepared medullar cavity of a long bone. Unlike the related art, nail assembly 200 of intramedullar device 50 may be manufactured in a wide range of diameters and lengths and is therefore suitable for a large variety of sizes of long bones, making intramedullar device 50 applicable to a wide range of patients.

In an embodiment of the present invention, nail assembly 200 is comprised of an outer tube 201 within which is seated an inner tube 202, as seen in FIG. 4. Long screw 112 runs down through the center length of both outer tube 201 and inner tube 202, connecting outer tube 201 to inner tube 202.

Outer tube 201 of the present invention may be anchored to the upper portion of the patient's bone by inserting, for example, pins or screws through at least two upper anchoring holes 203, as seen in FIG. 4.

Inner tube 202 moves longitudinally within outer tube 201 in a precise, stable manner. In some embodiments, the upper section of inner tube 202 may be guided within the lower section of outer tube 201 by means of a key system 207, wherein outer tube 201 has a channel and inner tube 202 has a protrusion that slides within said channel. Key system 207 ensures the smooth, stable, and precise longitudinal relative movement of inner tube 202, with no tolerance for any rotational movements that may cause instability of intramedullar device 50. According to some alternative embodiments, other suitable guiding systems may be employed.

According to an embodiment, long screw 112 enters the top of inner tube 202 and may be connected to inner tube 202 by, for example, matching threads on inner tube 202 and long screw 112. During the distraction phase, ratchet assembly 100 rotates long screw 112, which in turn pushes inner tube 202 down along key system 207, causing intramedullar device 50 to elongate.

An important feature of the present invention is an alignment hole 205, located at the lower end of inner tube 202. Alignment hole 205 comprises a bored out section of inner tube 202 that provides the doctor with a simple tool to ensure that intramedullar device 50 is correctly positioned within the bone, after insertion. Alignment hole 205 allows the doctor to adjust the alignment of nail assembly 200 by rotating intramedullar device 50 if required, into its correct position. When intramedullar device 50 is correctly aligned, alignment hole 205 will appear as a single circumference in the X-ray. This feature is important because intramedullar device 50 must be properly aligned to ensure that anchoring screws are inserted into the proper part of the bone, while preventing undue damage to the surrounding tissue.

Inner tube 202 of the present invention may also house at least one lower anchoring hole 204. Inner tube 202 may be anchored to the lower portion of the patient's bone by inserting, for example, pins or screws through at least one lower anchoring hole 204. After intramedullar device 50 is correctly aligned, alignment hole 205 may, according to some embodiments, further function as a hole for inserting additional anchoring screws.

According to some embodiments, there may be a plug 206 installed at the bottom most portion of inner tube 202 to seal inner tube 202. In other embodiments, inner tube 202 may be constructed as a single component.

The various components of intramedullar device 50 may be constructed from, for example, titanium alloys, stainless steel, or other acceptable materials for medical implanted devices.

Operation:

The bone is prepared, including performing the osteotomy, according to standard processes known to those who practice in the art. The present invention may then be inserted, as a single unit.

After nail assembly 200 is introduced into the bone, intramedullar device 50 must be aligned. Nail assembly 200 is slightly rotated around its longitudinal axis, until alignment hole 205 appears properly aligned on X-ray, that is, showing as a single circumference. This indicates that lower anchoring hole 204 and alignment hole 205 are properly positioned. It is important that when intramedullar device 50 is attached to the bone, each screw enter the bone in the proper location in order not to harm the surrounding blood vessels, tissues, and muscles in the area.

As soon as intramedullar device 50 is inserted in the bone and aligned, pins or screws may be inserted through upper anchoring hole 203, lower anchoring hole 204 and, optionally, alignment hole 205 in order to affix intramedullar device 50 in place. Center chamber 110 is then rotated in order to allow gear 111, and long screw 112 to rotate in the desired direction.

Once the length of intramedullar device 50 is adjusted and intramedullar device 50 is affixed to the bone, intramedullar device 50 is ready for use.

The user may activate intramedullar device 50, thereby elongating nail assembly 200, by depressing subcutaneous button 115 according to the instructions of the prescribing physician. Depressing subcutaneous button 115 presses center chamber 110 against leverage mechanism 107, causing leverage mechanism 107, in conjunction with pin 109, to rotate gear 111 the angle of one tooth. Gear 111 in turn rotates long screw 112 the same angle. When long screw 112 rotates, it causes inner tube 202 to slide longitudinally away from outer tube 201 and the remainder of nail assembly 200, effectively lengthening intramedullar device 50 and the bone.

Ratchet assembly 100 is geared so that a single depression of subcutaneous button 115 will cause long screw 112 to rotate a specific amount, which allows for very precise control of the extension activity.

After the distraction phase of the process is complete, a medical doctor may insert a needle through funnel shaped opening 113. Pressing the needle forces 102 cylindrical plate 104 to move forward, and allows the holes 103 on cylindrical plate 104 and holes 106 on center chamber 110 to align. Once holes 106 and 103 are aligned, ends 116 of locking spring 105 pop out through holes 106, as seen in FIG. 3. When locking spring 105 is positioned thusly, subcutaneous button 115 is prevented from further actuating leverage mechanism 107 and pin 109 or rotating long screw 112, thereby permanently locking entire ratchet assembly 100.

When the bone is sufficiently mended, intramedullar device 50 can be removed according to standard processes known to those who practice in the art.

While the above description contains many specifics, these should not be construed as limitations on the scope of the invention, but rather as exemplifications of the preferred embodiments. Those skilled in the art will envision other possible variations that are within the scope of the invention. Accordingly, the scope of the invention should be determined not by the embodiment illustrated, but by the appended claims and their legal equivalents.

What is claimed is:

1. An intramedullar distraction device for bone elongation based on the Callotasis phenomenon, which enables mechanical activation by a patient, said device comprising: a ratchet assembly including a ratchet cover, a gear and a long screw which rotates in an amount equivalent to at least one tooth on said gear for each ratchet action; a nail assembly that is rigidly connected to said ratchet assembly, wherein said nail assembly is adapted for installation within a prepared medullar cavity of a long bone, said nail assembly including at least two interconnected metal pieces, wherein rotation of said long screw of said ratchet assembly extends the nail assembly by altering a relative position of said at least two interconnected metal pieces; and a subcutaneous button located at said ratchet assembly for initiating said ratchet action by causing said gear to turn when said button is depressed, said button being activatable by pressure applied on to the skin.

2. The device of claim 1 wherein the ratchet assembly includes a center chamber, and a leverage mechanism having a first end and a second end, wherein the first end of said leverage mechanism is flexibly connected to the center chamber and the second end of said leverage mechanism contacts the gear upon actuation, such that upon depressing the subcutaneous button, the center chamber moves forward to actuate the leverage mechanism and cause the gear to rotate, whereas the gear rotation rotates the long screw.

3. The device of claim 2 further comprising a floating stopper mounted within said ratchet assembly between the leverage mechanism and the gear.

4. The device of claim 2 wherein the leverage mechanism includes a pin, wherein upon pushing the subcutaneous button, said pin contacts said gear.

5. The device of claim 2 wherein the center chamber includes a cylinder-plate that connects the subcutaneous button and a locking spring, wherein the cylinder-plate slides freely within the center chamber.

6. The device of claim 5, wherein the center chamber features an internal wall and wherein the cylinder plate includes at least two diametrically opposed holes and the locking spring sits inside said holes compressed against the internal wall of the center chamber thus holding the cylinder-plate in place.

7. The device of claim 6 further comprising a spacer located between a center chamber and the subcutaneous button for extending the subcutaneous button to accommodate the thickness of the fat and skin.

8. The device of claim 7, wherein said subcutaneous button features a terminal end, the device further comprising an opening located at the terminal end of said subcutaneous button and wherein the center chamber includes at least two holes which are aligned with the cylinder plate holes: wherein upon inserting a pin through the opening, the cylinder plates move forward, freeing the ends of the locking spring to move out into the center chamber holes, thus locking said ratchet mechanism.

9. The device of claim 2 wherein the leverage mechanism is a rocker-type mechanism that spans a gap between the center chamber and the gear.

10. The device of claim 2 wherein the ratchet assembly further comprises a floating mechanism mounted between the leverage mechanism and the gear that ensures that the gear can rotate in either a first direction or an opposite direction, causing the nail assembly to be shortened or elongated according to gear rotation direction.

11. The device of claim 1 wherein the nail assembly includes an outer tube, and an inner tube seated within the outer tube, wherein the long screw runs down through a center length of both the outer tube and the inner tube, connecting thereof.

12. The device of claim 11 wherein the outer tube has at least one hole enabling anchoring of said tube to the patient's bone.

13. The device of claim 11 wherein the outer tube includes a guiding system wherein said outer tube has a channel and said inner tube has a protrusion that slides within said channel, for supporting and guiding the inner tube movement.

14. The device of claim 11 wherein the inner tube and the long screw have matching threads enabling the inner tube to be connected to the long screw.

15. The device of claim 11 wherein the inner tube includes alignment holes which enable rotating and adjusting the device to a correct position within the bone.

16. The device of claim 11 wherein the inner tube has at least one hole enabling anchoring of said tube to the patients bone.

* * * * *